United States Patent [19]

Liotet et al.

[11] 4,342,747

[45] Aug. 3, 1982

[54] COLOSTRUM-BASED COMPOSITION FOR EXTERNAL USE

[76] Inventors: Serge Liotet, 12, rue Thibaud, 75014 Paris; Pierre-Jean Assier, 18, rue Lamarch, 75018 Paris, both of France

[21] Appl. No.: 163,189

[22] Filed: Jun. 26, 1980

[30] Foreign Application Priority Data

Jul. 2, 1979 [FR] France ............................ 79 17118

[51] Int. Cl.³ ............................................ A61K 35/12
[52] U.S. Cl. ............................................... 424/95
[58] Field of Search ............................................ 424/95

[56] References Cited

PUBLICATIONS

Adler's Physiology of the Eye (editor R. A. Moses (1975), pp. 18-21.
McClellan et al.-Am. J. of Ophthalmology, vol. 76, No. 1 (Jul. 1973), pp. 89-101.
Cochet et al.-Verres de Contact, vol. 11 (1966), pp. 7-14.
Korhonen-Chem. Abst., vol. 89 (1978), p. 104,451b.
Reiter-Chem. Abst., vol. 82 (1975), p. 119,471n.
Cassan et al.-Chem. Abst., vol. 88 (1978), p. 177,216t.
Oram et al.-Chem. Abst., vol. 88 (1969), p. 45107b.
Arima-Chem. Abst., vol. 57 (1962), p. 10460i.

*Primary Examiner*—Sam Rosen
*Attorney, Agent, or Firm*—Pearne, Gordon, Sessions, McCoy & Granger

[57] ABSTRACT

Colostrum-based compositions are disclosed. The compositions are for external ophthalmic use as a therapeutic agent and/or as a tear substitute.

4 Claims, 3 Drawing Figures

I  II  III  IV

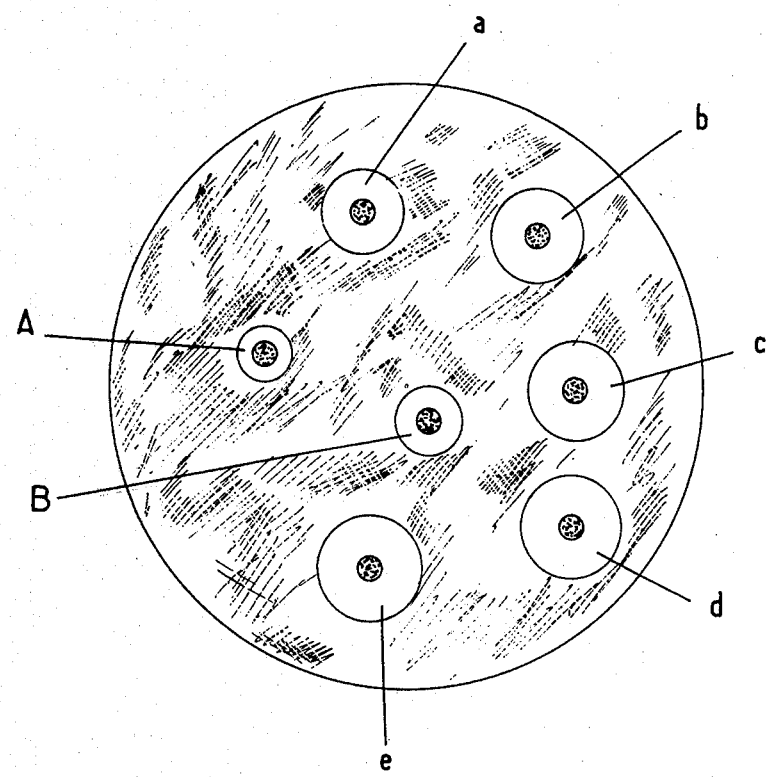

COLOSTRUM-BASED COMPOSITION FOR EXTERNAL USE

The present invention relates to novel colostrum-based compositions for external use.

Work carried out on the composition and the properties of colostrum have shown that common points exist between colostrum and tears.

Thus, the presence of lactotransferrin has been revealed in the same form as that to be found in tears. This protein represents, in tears, 40 to 50% of the total proteins and about 30% of the total bacteriostatic activity potentializing, furthermore, the activity of immunoglobulin A, also presents in tears. Moreover, lactotransferrin, an iron transporter, prevents the growth of micro-organisms by capturing in the medium the iron necessary for their metabolism. (work by G. SPIK and J. MONTREUIL, see, Spik, Formes Conjuguees Et Assimilation Du Lactofer Par Le Nourrisson, Annales De La Nutrition Et De La Alimention; 1971, 25, A 81-A 134 and Spik et al., Bacteriostasis of a milk-sensitive strain of Escherichia coli by immunoglobulins and iron-binding proteins in association, Immunology, 1978, 35, p. 663).

Figure 1:
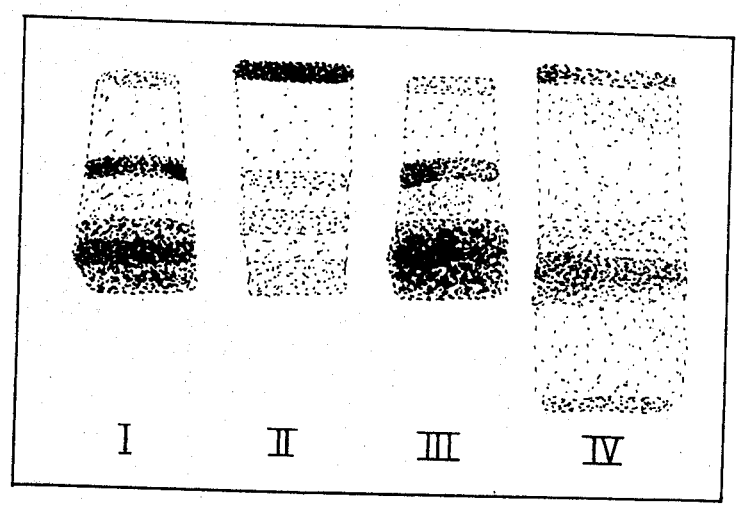
Figure 2:
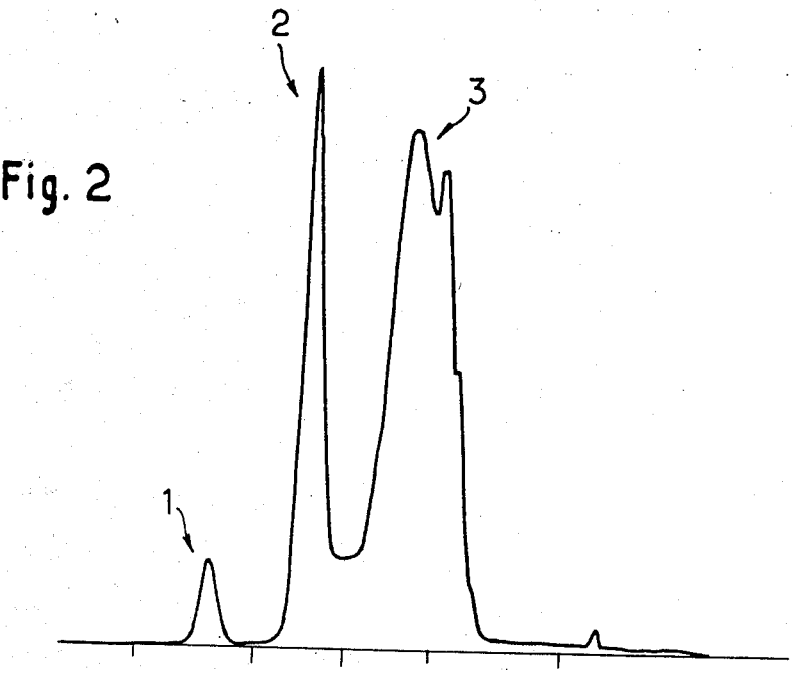

FIGS. 1 and 2 of the accompanying drawings show a reproduction, respectively, of the electrophoretic curve of colostrum (I and III) compared with that of serum (II) and with that of tears (IV), and a photometric recording of a colostrum electrophoresis. In this figure 2, peaks 1, 2 and 3 show the presence of serumalbumin, lactoglobulin and lactotransferrin.

Other information as to the composition of colostrum is given in the table below.

The revelation of these common points between colostrum and tears has led to the study of possible applications of colostrum, particularly in the field of ophtalmology where a demand exists for therapeutic and/or tear substitution preparations.

In fact, the existing compositions present for the most part one or more of the following disadvantages:
they induce, like methylcellulose, a deformation of images,
their pH or their isotonicity is ill-adjusted,
it is necessary to instil them frequently,
they only offer a few points of comparison with tears.

The colostrum-based compositions may be used as:
a tear-substitution product, in hyposecretions, dry syndromes and for the wearers of contact lenses: in fact, brought to an appropriate dilution, colostrum has a pH of 7.0 and a protein concentration, so an oncotic pressure, close to that of tears;
antiseptic: because of the presence of lactotransferrin and immunoglobulins A, G and M;
anti-inflammatory and anticollagenasic: because of the presence of Alpha 1 antitrypsin whose anti-inflammatory and anticollagenasic activites are known;
trophic and cicatrizant: because of the supply of nutritive substances for the tissues, i.e. proteins, sugars, amino-acids and numerous hydrosoluble vitamins contained in this liquid, namely vitamins B1, B2 B12, C, nicotinic acid, pantothenic acid, biotin, folic acid.

The bacteriostatic activity of colostrum has been tested on Micrococcus lysodeikticus, in relation to the inhibiting activity of lysozyme, the principal bacteriolytic agent of tears. FIG. 3 of the accompanying drawings shows a reproduction of a Petri box culture on a Mueller-Hinton medium. The inhibition zones A and B were caused by the presence of 2 µl and 5 µl of colostrum. Inhibition zones a, b, c, d and e were caused by the presence, respectively of 1, 2, 3, 4 and 5 g/l of a lysozyme solution used as a reference.

Comparing the inhibition zones and knowing that the square of the inhibition diameter is directly proportional to the concentration of the inhibiting substance, it may be considered that the bacteriostatic activity of colostrum, at the concentrations used, is about equivalent to that of a 0.5 g/l lysozyme solution.

Other applications may also be considered for colostrum. Thus, taking into account its extreme richness in liposoluble vitamins A, D and E and its trophic and cicatrizant action on the skin and on the mucous membranes, colostrum may form the active principal of creams or ointments used in dermatology or cosmetology.

The following examples are given, in a way which is in no wise limiting, to illustrate the invention.

EXAMPLE 1

Preparation of an eye lotion

Milk-bank or dairy colostrum was creamed, by centrifugation at 5000 rpm for 15 minutes and the floating matter comprising the cream and the residue formed of cellular waste was eliminated, so as to keep only the intermediate phase. This intermediate phase was then sterilized by subjecting it to ionizing radiation, then it was lyophilized. At the time of using, the lyophilate was dissolved and brought to an appropriate dilution by addition of a diluant such that the resulting composition had the pH and the isotonicity of tears. Since colostrum is a natural product, its quantitative composition is not absolutely constant. If need be, this composition can be brought within pre-determined norms by giving to the dilution solution an appropriate composition.

EXAMPLE 2

Preparation of an eye lotion

Creamed colostrum was diluted to ⅓ with physiological serum and 0.1% sodium mercurothiolate was added thereto a preservative. The composition may be made hypertonic or hypotonic with respect to tears depending on the desired effect. Instead of sodium mercurothiolate, any other appropriate conserving agent could be used, among others, a mixture of soda-containing propyl and methyl p-hydroxybenzoate used for example at a concentration of 2.66 per 1000 of methyl derivative and 1.33 per 1000 of propyl derivative, chlorhexidine gluconate used for example at a concentration of 0.054 per 1000 and possibly associated with calcic EDTA for example at a concentration of 3 per 1000, or else a boric acid/sodium borate mixture at a concentration of 10 per 1000 of boric acid and 2.5 per 1000 of borate.

EXAMPLE 3

Preparation of an eye lotion

An eye lotion was prepared as in example 1 or 2 and, before sterilization, 1.5 g/l of lactotransferrine was added thereto. The resulting composition was sterilized by tindallization or was pasteurized.

EXAMPLE 4

Preparation of an ointment

Milk-bank or dairy colostrum was creamed, concentrated by appropriate techniques and presented in the form of an ointment, with possible addition of neutral stabilizing elements, other active ingredients or transcutaneous passage agents, with a view to its use in ophtalmology, dermatology or cosmetology.

EXAMPLE 5

Clinical cases (a) Mrs. J. H., 62 years old. The patient had suffered for five months from an ulcer of the cornea resisting all the therapeutics used. Complete cicatrization was obtained in 10 days by instillation of colostrum eye lotion, 4 times a day.

(b) Mr. A. A., 53 years old. The patient presented a dry syndrom little improved, or not at all, by physiological serum or methyl cellulose eye lotions. The instillation, 4 times a day, of colostrum eye lotion removed the keratalgies, the stinging sensations and restored to him normal comfort.

(c) Mr. A. L., 72 years old. The patient presented a dry betablocking post-therapeutic syndrom. He had the sensation of a foreign body and burning. The rupture of the lacrymal film was immediate. As soon as colostrum eye lotion was instilled, the subjective troubles ceased. A check showed the re-establishment of a good lacrymal film.

TABLE

COMPOSITION OF COLOSTRUM

|  | Average composition according to literature | Composition of a sample (1000 ml) of human creamed colostrum |
|---|---|---|
| Sodium | 50.1 mEq | 35 mEq |
| Potassium | 74.5 mEq | 35 mEq |
| Calcium | 481 mg/l | 392 mg/l |
| Phosphorous | 157 mg/l | 84.5 mg/l |
| Chlorine | 586 mg/l | 355 mgl/ |
| Magnesium | 42 mg/l | 107 mg/l |
| Iron | 40 μg/l |  |
| Copper | 40 μg/l |  |
| Total proteins | 22.9 g/l | 21.5 g/l |
| IgA |  | 1.5 g/l |
| IgG |  | 0.13 g/l |
| IgM |  | 0.45 g/l |
| C'3 |  | 0.15 g/l |
| Serumalbumin |  | 0.70 g/l |
| Transferrin |  | 1.70 g/l |
| Orosomucoid |  | 0 |
| Alpha 1 antitrypsin |  | 0.125 g/l |
| Alpha 2 macroglobulin |  | 0 |
| Lactotransferrin |  | 1.35 g/l |
| Urea |  | 0.38 g/l |
| Uric acid |  | 22 mg/l |
| Reducing sugars |  | 119 g/l |
| Glucose |  | 0.50 g/l |
| Lactose | 57 g/l |  |
| Total lipids | 29.50 g/l | 5.85 g/l |
| Cholesterol |  | 0.66 g/l |
| Triglycerides |  | 1.40 g/l |
| SERO DIAGNOSIS |  |  |
| Herpes |  | titer: 0 |
| Toxoplasmose |  | titer: 5 UI/ml |
| Rubella |  | titer less than 8 |
| TPHA |  | NEGATIVE |
| VITAMINS |  |  |
| B1 |  | 19 μg/l |
| B2 |  | 302 μg/l |
| B12 |  | 0.45 μg/l |
| C |  | 72 mg/l |
| E |  | 14.8 μg/l |
| Nicotinic acid |  | 750 μg/l |
| Pantothenic acid |  | 1.83 mg/l |
| Biotin |  | 0.6 μg/l |
| Folic acid |  | 0.5 μg/l |

In summary, the similarities or common points between colostrum and tears have been utilized herein to provide novel colostrum-based compositions for external ophthalmic use. As required, a colostrum-based composition may be prepared having a colostrum protein concentration ranging in value close to that of human tears. Ointment compositions may be prepared by concentrating creamed colostrum. Eye lotion compositions are provided by dilution of creamed colostrum to $\frac{1}{3}$ of its protein concentration, and effective treatment is provided by periodic dropwise application to the eye (e.g., 4 times a day).

What is claimed is:

1. A composition for external ophthalmic use as a therapeutic agent and/or a tear substitute, characterized in that it contains colostrum as an active ingredient in an effective amount in an eye lotion carrier or in an ointment carrier.

2. The composition as claimed in claim 1, characterized in that the colostrum is creamed.

3. The composition as claimed in claim 1 or 2, characterized in that it contains an amount of colostrum effective for giving the composition a content in colostrum proteins of approximately that of human tears.

4. The composition as claimed in claim 2, characterized in that said creamed colostrum is diluted to $\frac{1}{3}$ by addition of a diluant.

* * * * *